United States Patent [19]

Bushell

[11] Patent Number: 4,714,790

[45] Date of Patent: Dec. 22, 1987

[54] FLUORO ALCOHOLS AND INSECTICIDAL ESTERS THEREOF

[75] Inventor: Michael J. Bushell, Wokingham, England

[73] Assignee: Imperial Chemical Industries PLC, London, England

[21] Appl. No.: 897,345

[22] Filed: Aug. 18, 1986

[30] Foreign Application Priority Data

Sep. 13, 1985 [GB] United Kingdom ............... 8522656

[51] Int. Cl.$^4$ ............................................. C07B 49/00
[52] U.S. Cl. ................................... 568/807; 560/124; 568/812
[58] Field of Search ................. 568/807, 812; 560/124

[56] References Cited

U.S. PATENT DOCUMENTS 4,405,640 9/1983 Punja .................................. 568/812

FOREIGN PATENT DOCUMENTS 3145286 5/1983 Fed. Rep. of Germany ...... 568/812

OTHER PUBLICATIONS

I. L. Finar, "Organic Chemical" (vol. 1), Longmans, Green and Co. (1959), p. 333.

Primary Examiner—Michael L. Shippen
Attorney, Agent, or Firm—Cushman, Darby & Cushman

[57] ABSTRACT

The invention concerns a process for preparing 2-substituted-3,4,5,6-tetrafluorobenzyl alcohols by reaction of pentafluorobenzyl alcohol with a Grignard reagent under specified conditions. The products some of which are novel are useful as intermediates for insecticidal esters e.g. those with pyrethroid acids. A typical ester is 2-methyl-3,4,5,6-tetrafluorobenzyl 3-(2-chloro-3,3,3-trifluoroprop-1-en-1-yl)-2,2-dimethylcyclopropane carboxylate.

1 Claim, No Drawings

FLUORO ALCOHOLS AND INSECTICIDAL ESTERS THEREOF

This invention relates to novel fluoro substituted benzyl alcohols and insecticidal esters thereof and to methods of preparing said alcohols and esters.

In a first aspect the invention provides a process of preparing a 2-substituted-3,4,5,6-tetrafluorobenzyl alcohol of formula:

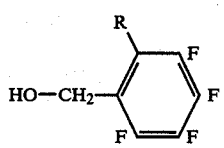

wherein R is an alkyl or alkenyl group of up to 6 carbon atoms or an aryl group of up to 10 carbon atoms, which comprises reacting pentafluorobenzyl alcohol with an appropriate Grignard reagent of formula R—Mg—X where X is halogen, wherein the Grignard reagent is slowly added to an excess of the pentafluorobenzyl alcohol and the temperature of the reaction is maintained at or below 40° C. during the addition.

The process when performed in this way leads unexpectedly to the selective formation of the required 2-substitued-3,4,5,6-tetrafluorobenzyl alcohols with little or no production of either the isomeric 4-substituted-2,3,4,5,6-tetrafluorobenzyl alcohols and in apparent absence of the expected Zerewitanoff reaction whereby the alcohol reacts with the Grignard reagent as follows:

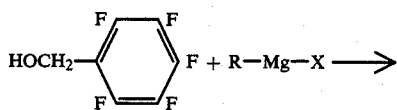

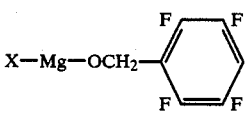

Typical examples of alcohols which can be prepared by the process of the invention include
2-methyl-3,4,5,6-tetrafluorobenzyl alcohol
2-ethyl-3,4,5,6-tetrafluorobenzyl alcohol
2-n-propyl-3,4,5,6-tetrafluorobenzyl alcohol
2-n-butyl-3,4,5,6-tetrafluorobenzyl alcohol
2-n-hexyl-3,4,5,6-tetrafluorobenzyl alcohol
2-i-butyl-3,4,5,6-tetrafluorobenzyl alcohol
2-allyl-3,4,5,6-tetrafluorobenzyl alcohol
2-(but-2-en-1-yl)-3,4,5,6-tetrafluorobenzyl alcohol
2-phenyl-3,4,5,6-tetrafluorobenzyl alcohol
2-(2-methylphenyl)-3,4,5,6-tetrafluorobenzyl alcohol
2-(2,4-dimethylphenyl)-3,4,5,6-tetrafluorobenzyl alcohol In a further aspect therefore the invention provides novel compounds of formula I wherin R is as defined hereinabove. The compounds of formula I are particularly useful as intermediates for the preparation of pesticides, especially pyrethroid insecticides of formula:

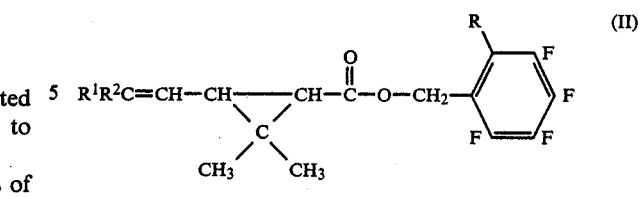

wherein R is as defined hereinabove and $R^1$ and $R^2$ are each selected from methyl, trifluoromethyl, fluoro, chloro and bromo. Preferably, either $R^1$ is chloro or fluoro and $R^2$ is trifluoromethyl or $R^1$ and $R^2$ are the same and are both chloro or both bromo.

In a yet further aspect therefore the invention provides novel pyrethroid esters of formula II wherein R, $R^1$ and $R^2$ are as defined hereinabove.

Typical pyrethroid esters of formula II include:
2-methyl-3,4,5,6-tetrafluorobenzyl (+)-cis/trans-3-(Z-2-chloro-3,3,3-trifluoroprop-2-en-2-yl)-2,2-dimethylcyclopropane carboxylate, and the corresponding (+)-cis isomer thereof; 2-allyl-3,4,5,6-tetrafluorobenzyl (+)-cis/trans-3-(Z-2-chloro-3,3,3-trifluoroprop-2-en-2-yl)-2,2-dimethylcyclopropane carboxylate, and the corresponding (+)-cis isomer thereof; 2-(2-methylphenyl)-3,4,5,6-tetrafluorobenzyl (+)-cis/trans-3-(Z-2-chloro-3,3,3-trifluoroprop-2-en-2-yl)-2,2-dimethylcyclopropane carboxylate, and the corresponding (+)-cis isomer thereof; and 2-methyl-3,4,5,6-tetrafluorobenzyl (+)-cis/trans-3-(2,2-dichlorovinyl)-2-dimethylcyclopropane carboxylate, and the corresponding (+)-cis isomer thereof.

The pyrethroid esters of formula II are esters and may be prepared by conventional esterification processes, of which the following are examples.

(a) An acid of formula

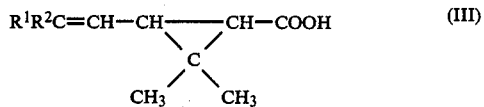

where X has any of the meanings given hereinabove, may be reacted directly with a 2-substituted-3,4,5,6-tetrafluorobenzyl alcohol of formula I the reaction preferably taking place in the presence of an acid catalyst, for example, dry hydrogen chloride, or a dehydrating agent, for example, a carbodiimide such as dicyclohexylcarbodiimide.

(b) The acid halide derived from the acid of formula III where Hal represents a halogen atom, preferably a chlorine atom, and X has any of the meanings given hereinabove, may be reacted with the alcohol of formula III, the reaction preferably taking place in the presence or a base, for example, pyridine, trialkylamine alkali metal hydroxide or carbonate, or alkali metal alkoxide.

(c) The lower alkyl ester derived from the acid of formula III preferably the methyl or ethyl ester, is heated with the alcohol of formula I to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvent and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula III. These may be obtained by conventional isomer separation techniques from mixtures of isomers. Thus cis and trans isomers may be separated by fractional cystallisation of the caboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula I to produce a compound of formula II in the form of an individually pure isomer thereof.

The compounds of formula II may be used to combat and control infestations of insect pests and also other invertebrate pests, for example, acarine pests. The insect and acarine pets which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-biollethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion o diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemyins, for example such as abamectin, avermectin, and milbemycin;

(g) Hormones such as juvenile hormone, juvabione, or ecdysones.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of the rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl pheno, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
*Aonidiella spp.* (scale insects)
*Trialeuroides spp.* (white flies)
*Blattella germanica* (cockroaches)
*Spodoptera littoralis* (cotton leaf worm)
*Heliothis virescens* (tobacco budworms)
*Chortiocetes terminifera* (locusts)
*Diabrotica spp.* (rootworms)
*Agrotis spp.* (cutworms)
*Chilo partellus* (maize stem borers)
*Nilaparvata lugens* (plant hoppers)

The compounds are particularly useful for the control of insect pests which inhabit the soil including *Argrotis spp, Agriotis spp* and *Diabrotica spp*. For this purpose they are preferably formulated as granules in which the insecticidally active esters are supported (e.g. by coating or impregnation) or mineral, e.g. pumice or gypsum, granules, or granules of vegetables matter e.g. those derived from corn cobs. They are applied to soil at rates of 0.05 to 25 kg/ha (based on active ingredient), and preferably at rates of 0.1 to 15 kg/ha. Because the invention compounds have high intrinsic activity against the pests and are also capable of exerting this acitivity over a prolonged period only one application is required in the course of a growing season th give effective control. The granules may contain from 0.5 to 2.5% by weight of the active ingredient, and the stability of the granules may be improved and the rate of release of the active ingredient may be regulated by the incorporation of a resin or coating with a polymeric substance e.g. a polyvinyl alcohol based material. The granules may be applied to the surface of the soil adjacent to the furrow in which the plants are growing, and may be lightly incorporated in the soil thereafter, or the granules may be placed in the furrows with the seed at the time of planting.

The various aspects of the invention are illustrated by the following examples.

EXAMPLE 1

This Example illustrates the preparation of 2-methyl-3,4,5,6-tetrafluorobenzyl alcohol.

A solution of methyl bromide (9.6 g) in dry tetrahydrofuran (25 cm$^3$) was added dropwise in a stirred mixture of magnesium turnings (5.0 g), dry tetrahydrofuran (50 cm$^3$) and a small crystal of iodine at the ambient temperature (ca. 22° C.). When the addition was complete the mixture was stirred for a further 1 hour at the ambient temperature and the solution of methyl magnesium bromide thus formed was then added dropwise to a stirred solution to pentafluorobenzyl alcohol (17.8 g) in tetrahydrofuran (50 cm$^3$) whilst the temperature was maintained at 30° C. When the addition was complete the mixture was stirred for a further 2 hours at the ambient temperature and for 3 hours at the reflux temperature. Water at 0° C. was added to the mixture, which was then acidified with dilute hydrochloric acid and extracted with diethyl ether (2×80 cm$^3$). The extracts were combined, washed with water, dried over anhydrous magnesium sulphate and concentrated by evaporation of the solvent under reduced pressure. The residual oil (4.6 g) was shown by gas liquid chromatographic examination of a sample to consist of ca. 70% by weight of unreacted starting material and ca. 30% by weight of product. The oil was subjected to vigorous purification by column and thin-layer chromatography using a silica gel support and eluting with a mixture of diethyl ether and hexane (3:7 by volume), to obtain 2-methyl-3,4,5,6-tetrafluorobenzyl alcohol as a colourless oil.

$^1$H nmr (CDCl$_3$) δ: 1.86 (broad s,1H); 2.35 (q,3H); 4.74 (d,2H).

$^{19}$F nmr (CDCl$_3$) δ: −142.3 (dd, J=12.6, 21Hz); −145.9 (dd, J=12.6, 21Hz); −157.25 (t,J=21Hz); −160.5 (t,J=21Hz);

EXAMPLE 2

This Example illustrates the preparation of 2-methyl-3,4,5,6-tetrafluorobenzyl (+)-cis-3-(Z-2-chloro-3,3,3-trifluoroprop-1-en-1-yl)-2,2-dimethylcyclopropane carboxylate.

A mixture of (+)-cis-3-(Z-2-chloro-3,3,3-trifluoroprop-1en-1-yl)-2,2-dimethylcyclopropane carboxylic acid (190 mg ), and thionyl chloride (3.0 cm$^3$) was heated at the reflux temperature for 30 minutes after which the excess thionyl chloride was removed by distillation under reduced pressure, the final traces being removed by azeotropic distillation with toluene. The resultant acid chloride was added to a mixture of 2-methyl-3,4,5,6-tetrafluorobenzyl alcohol (150 mg ), pyridine (180 mg ) toluene (8.0 cm$^3$) and the mixture stirred at the ambient temperatue for 2 hours. The mixture was diluted with water and extracted with chloroform. The extracts were dried over anhydrous magnesium sulphate and concentrated by evaporation of the solvent. The residual oil was purified by chromatography on a silica gel column eluted with chloroform to yield 2-methyl-3,4,5,6-tetrafluorobenzyl (+)-cis-3-(Z-2-chloro-3,3,3-trifluoroprop-1en-1-yl)-2,2-dimethylcyclopropane carboxylate as an oil (110 mg ).

$^1$H nmr (CDCl$_3$) δ: 1.35 (s,6H); 1.95–2.4 (m,5H); 5.26 (d,2H); 7.0 (d,1H).

I claim:

1. A process for preparing a compound of formula:

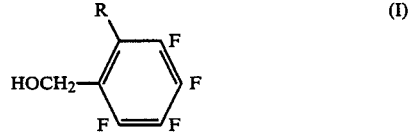

wherein R is alkyl or alkenyl of up to 6 carbon atoms or aryl of up to 10 carbon atoms which comprises reacting pentafluorobenzyl alcohol with a Grignard reagent of formula R—Mg—X where X is halogen, wherein the Grignard reagent is added slowly to an excess of the pentafluorobenzyl alcohol and the temperature of the reaction is maintained at or below 40° C. during the addition.

* * * * *